US00PP14183P29

(12) United States Plant Patent
Watanabe et al.

(10) Patent No.: US PP14,183 P2
(45) Date of Patent: Sep. 30, 2003

(54) PETUNIA PLANT NAMED 'KIRIMAJI DOUBLE BLUE VEIN'

(50) Latin Name: *Petunia hybrida*
Varietal Denomination: Kirimaji Double Blue Vein

(75) Inventors: Saori Watanabe, Ujiie-machi (JP); Daigaku Takeshita, Utsunomiya (JP)

(73) Assignee: Kirin Brewery Company Ltd., Tokyo (JP)

( * ) Notice: Subject to any disclaimer, the term of this patent is extended or adjusted under 35 U.S.C. 154(b) by 0 days.

(21) Appl. No.: 10/259,967

(22) Filed: Sep. 29, 2002

(51) Int. Cl.[7] ..... A01H 5/00
(52) U.S. Cl. ..... Plt./356
(58) Field of Search ..... Plt./356

(56) References Cited

U.S. PATENT DOCUMENTS

PP13,398 P2 * 12/2002 Watanbe et al. ..... Plt./356

OTHER PUBLICATIONS http://www.inspection.gc.ca/english/plaveg/pbrpov/cropreport/pet/app00003927e.shtml.* http://www.greenhousegrower.com/packtrials/v–show003.html.* http://www.ecke.com/html/h_fields/prodpages/ff_doubl_blustar.html.*

UPOV ROM GTITM Computer Database, GTI JOUVE retrieval software 2002/06 citation(s) for "Kirimaji Double Blue Vein" and "Danbblst".*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Petunia plant named 'Kirimaji Double Blue Vein', characterized by its low mounding cascading to prostrate plant habit; freely branching growth habit; early and freely flowering habit; light violet-colored semi-double flowers with dark violet-colored venation; and good weather tolerance.

2 Drawing Sheets

Botanical classification/cultivar designation: *Petunia hybrida* cultivar Kirimaji Double Blue Vein.

BACKGROUND OF THE INVENTION

The present Invention relates to a new and distinct cultivar of Petunia plant, botanically known as *Petunia hybrida,* and hereinafter referred to by the name 'Kirimaji Double Blue Vein'.

The new Petunia is a product of a planned breeding program conducted by the Inventors in Tochigi, Japan. The objective of the breeding program is to create new double Petunia cultivars that have stronger growth and attractive flower coloration.

The new Petunia originated from a cross-pollination made by the Inventors in June, 2000, in Tochigi, Japan, of the Petunia cultivar Kirimaji Double Pink Vein, disclosed in U.S. Plant Pat. No. 13,398, as the female, or seed, parent with the Petunia cultivar Surfinia Super Double Vein, not patented, as the male, or pollen, parent. The new Petunia was discovered and selected by the Inventors as a single flowering plant within the progeny of the stated cross-pollination grown in a controlled environment in Tochigi, Japan, in November, 2000. The selection of this plant was based on its strong plant growth habit and attractive flower coloration.

Asexual reproduction of the new cultivar by terminal cuttings taken in a controlled environment in Tochigi, Japan, since November, 2000, has shown that the unique features of this new Petunia are stable and reproduced true to type in successive generations.

SUMMARY OF THE INVENTION

Plants of the cultivar Kirimaji Double Blue Vein have not been observed under all possible environmental conditions. The phenotype may vary somewhat with variations in environment such as temperature and light intensity without, however, any variance in genotype.

The following traits have been repeatedly observed and are determined to be the unique characteristics of 'Kirimaji Double Blue Vein'. These characteristics in combination distinguish 'Kirimaji Double Blue Vein' as a new and distinct cultivar of Petunia:

1. Low mounding cascading to prostrate plant habit.
2. Freely branching growth habit.
3. Early and freely flowering habit.
4. Light violet-colored semi-double flowers with darker violet-colored venation.
5. Good weather tolerance; tolerant to wind, rain, and low and high temperatures.

Plants of the new Petunia can be compared to plants of the female parent, the cultivar Kirimaji Double Pink Vein. In side-by-side comparisons conducted by the Inventors in Tochigi, Japan, plants of the new Petunia differed from plants of the female parent primarily in flower color.

Plants of the new Petunia can be compared to plants of the male parent, the cultivar Surfinia Super Double Vein. In side-by-side comparisons conducted by the Inventors in Tochigi, Japan, plants of the new Petunia differed from plants of the cultivar Surfinia Super Double Vein primarily in flower form and size as plants of the new Petunia had slightly smaller and more double flowers than plants of the cultivar Surfinia Super Double Vein.

Plants of the new cultivar can be compared to plants of the cultivar Doubloon Blue Star, not patented. In side-by-side comparisons conducted by the Inventors in Tochigi, Japan, plants of the new Petunia differed from plants of the cultivar Doubloon Blue Star in the following characteristics:

1. Plants of the new Petunia had slightly smaller flowers than plants of the cultivar Doubloon Blue Star.
2. Plants of the new Petunia flowered earlier than plants of the cultivar Doubloon Blue Star.
3. Petal apices of plants of the new Petunia were rounded whereas petal apices of plants of the cultivar Doubloon Blue Star were pointed.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Petunia.

The photograph on the first sheet comprises a side perspective view of a typical flowering plant of 'Kirimaji Double Blue Vein'. The photograph on the second sheet comprises a close-up view of a typical flower of 'Kirimaji Double Blue Vein'.

DETAILED BOTANICAL DESCRIPTION

In the following description, color references are made to The Royal Horticultural Society Colour Chart except where general terms of ordinary dictionary significance are used. Plants used for the aforementioned photographs and the following description were grown in containers and under conditions which closely approximate commercial production conditions during the spring in Santa Paula, Calif. in a polyethylene-covered greenhouse. Plants used for the photographs and the description were about nine weeks from planting rooted young plants. During the production period, day temperatures ranged from 20 to 35° C., night temperatures ranged from 10 to 20° C., and light levels ranged from 20 to 40 kilolux.

Botanical classification: *Petunia hybrida* cultivar Kirimaji Double Blue Vein.

Parentage:

*Female, or seed, parent.*—*Petunia hybrida* cultivar Kirimaji Double Pink Vein, disclosed in U.S. Plant Pat. No. 13,398.

*Male, or pollen, parent.*—*Petunia hybrida* cultivar Surfinia Super Double Vein, not patented.

Propagation:

*Type cutting.*—Terminal vegetative cuttings.

*Time to initiate roots.*—Summer: About 3 days at 25° C. Winter: About 5 days at 23° C.

*Time to produce a rooted young plant.*—Summer: About 21 days at 25° C. Winter: About 23 days at 25° C.

*Root description.*—Fine, fibrous, and white in color.

*Rooting habit.*—Freely branching; dense.

Plant description:

*Form.*—Annual flowering plant; low mounding cascading to prostrate plant habit; dense and bushy appearance.

*Plant height* (*from soil level to top of plant plane*).—About 12 cm.

*Plant diameter* (*area of spread*).—About 58 cm.

*Growth rate.*—Relatively rapid.

*Branching habit.*—Freely basal branching, about 28 lateral branches per plant; lateral branches develop at potentially every node; pinching is typically not required.

*Lateral branch description.*—Length: About 34 cm. Diameter: About 3.5 mm. Internode length: About 0.8 to 2.5 cm. Orientation: Initially upright, then horizontal. Texture: Pubescent; short, fine hairs. Strength: Strong, but flexible. Color: 144A.

*Foliage description.*—Leaves simple, generally symmetrical. Arrangement: Alternate before flowering, then opposite. Length: About 3.7 cm. Width: About 3.2 cm. Shape: Broadly elliptic to oval. Apex: Rounded. Base: Acute. Margin: Entire. Texture, upper and lower surfaces: Viscid, glandular; slightly pubescent. Venation pattern: Pinnate; arcuate. Color: Young foliage, upper surface: 146A. Young foliage, lower surface: 146B. Fully expanded foliage, upper surface: 147A. Fully expanded foliage, lower surface: 146B. Venation, upper surface: 146C. Venation, lower surface: 146D. Petiole length: About 1 cm. Petiole diameter: About 2.5 mm. Petiole color: 144B.

Flower description:

*Flower type and habit.*—Flowers face upright or outward; semi-double flower form; solitary and axillary; salverform. Freely flowering habit, about 14 to 18 flowers and flower buds per lateral stem. Flowers persistent.

*Fragrance.*—Moderate; sweet, floral.

*Natural flowering season.*—Spring until frost in the autumn; flowering continuous during this period.

*Time to flower.*—Early flowering; plants begin flowering about 2 weeks after planting.

*Flower longevity on the plant.*—About 10 days.

*Flower size.*—Diameter: About 5 cm. Length (height): About 3.5 cm. Tube length: About 2.2 cm. Tube diameter, base: About 4 mm.

*Flower buds* (*showing color*).—Length: About 3 cm. Diameter: About 1 cm. Shape: Obovate. Color: 83A to 83B.

*Corolla.*—Arrangement/appearance: Outer whorl of about six to eight petals fused at base and surrounding inner whorl of about 14 petals. Petal length, outer and inner whorls of petals: About 1.7 cm. Petal width: Outer whorl of petals: About 1.9 cm. Inner whorl of petals: About 1.75 cm. Petal shape: Spatulate. Petal apex: Rounded. Petal margin: Entire. Petal texture: Smooth, glabrous; velvety. Petal surface: Ruffled. Color: Petal, when opening, upper surface: 82D; venation, 83B. Petal, when opening, lower surface: 85B; venation, 83A. Petal, opened flower, upper surface: 84C; color fading to slightly to closer to 84D with subsequent development; venation, 83B to 83C. Petal, opened flower, lower surface: 84D; venation, 83A to 83B. Flower throat (inside): 83A; venation, 83D. Flower tube (outside): 83A; venation, more gray than 83A.

*Sepals.*—Arrangement/appearance: Single whorl of five sepals fused at base; star-shaped. Length: About 1 cm. Width: About 2 mm. Shape: Narrowly elliptic. Apex: Rounded. Margin: Entire. Texture, upper and lower surfaces: Slightly coarse; pubescent. Color: Upper surface: 146B. Lower surface: 146C.

*Peduncles.*—Length: About 1.5 cm. Width: About 1 mm. Strength: Strong. Angle: About 45° from stem. Texture: Pubescent. Color: 146A.

*Reproductive organs.*—Stamens: Quantity: About 12 to 14 per flower. Anther shape: Oval. Anther size: About 2 mm by 2.5 mm. Anther color: 156A. Pollen amount: Scarce. Pollen color: 188B. Pistils: Quantity: One per flower. Pistil length: About 1.2 cm. Stigma shape: Anvil-shaped. Stigma color: 147A. Style length: About 4 mm. Style color: 147C. Ovary color: 144A.

*Seed/fruit.*—Seed and fruit production has not been observed.

Disease/pest resistance: Plants of the new Petunia have not been noted to be resistant to pathogens and pests common to Petunia.

Weather/temperature tolerance: Plants of the new Petunia are tolerant to rain and wind and have been observed to tolerate temperatures from 3 to 35° C.

It is claimed:

1. A new and distinct cultivar of Petunia plant named 'Kirimaji Double Blue Vein', as illustrated and described.

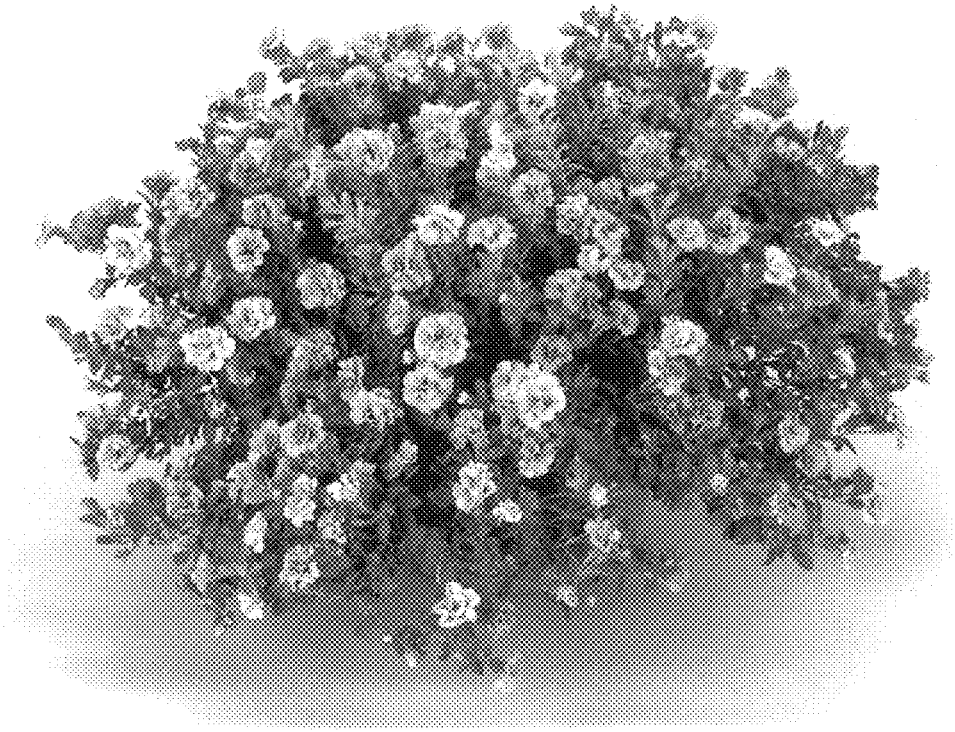

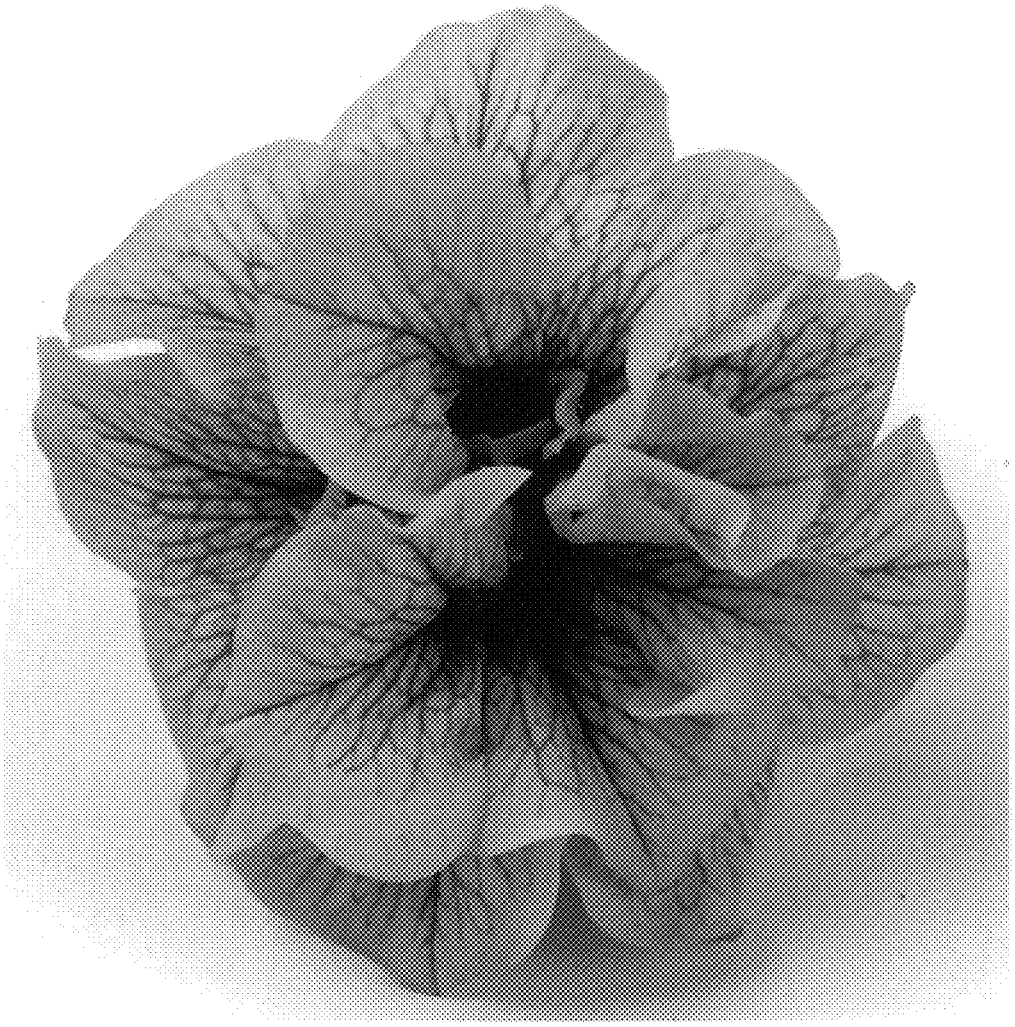

* * * * *